(12) United States Patent
Tovar Lopez

(10) Patent No.: US 8,376,927 B2
(45) Date of Patent: Feb. 19, 2013

(54) FLUID PUMPING VENTRICULAR ASSIST DEVICE AND COMPONENTS WITH STATIC SEAL

(75) Inventor: Francisco Javier Tovar Lopez, Mexico City (MX)

(73) Assignee: Vitalmex Internacional S.A. De S.V., Mexico City (MX)

( * ) Notice: Subject to any disclaimer, the term of this patent is extended or adjusted under 35 U.S.C. 154(b) by 948 days.

(21) Appl. No.: 12/412,300

(22) Filed: Mar. 26, 2009

(65) Prior Publication Data

US 2009/0264697 A1     Oct. 22, 2009

Related U.S. Application Data

(60) Provisional application No. 61/040,615, filed on Mar. 28, 2008.

(51) Int. Cl.
*A61N 1/362* (2006.01)
(52) U.S. Cl. .......................................... 600/16; 623/3.16
(58) Field of Classification Search .................... 600/16; 623/3.1, 3.18, 3.21; 417/53, 56
See application file for complete search history.

(56) References Cited

U.S. PATENT DOCUMENTS

| | | | |
|---|---|---|---|
| 3,208,448 A | 9/1965 | Woodward et al. | |
| 3,919,722 A * | 11/1975 | Harmison | 623/3.16 |
| 4,427,470 A * | 1/1984 | Kolff | 156/73.1 |
| 4,723,948 A | 2/1988 | Clark et al. | |
| 4,902,291 A | 2/1990 | Kolff et al. | |
| 6,949,065 B2 * | 9/2005 | Sporer et al. | 600/16 |
| 7,217,236 B2 | 5/2007 | Calderon et al. | |
| 2004/0242954 A1 * | 12/2004 | Calderon et al. | 600/16 |
| 2008/0027536 A1 * | 1/2008 | Azzolina | 623/3.21 |

FOREIGN PATENT DOCUMENTS

EP     1629855     3/2006

OTHER PUBLICATIONS

International Search Report and Written Opinion of PCT/MX2009/000029.

* cited by examiner

*Primary Examiner* — Carl H Layno
*Assistant Examiner* — Paula J Stice
(74) *Attorney, Agent, or Firm* — Ladas & Parry LLP

(57) ABSTRACT

A ventricular assist device (VAD) having static seal structure for a pump housing which includes a support structure, a first sealing element, and a second sealing element. The support structure circumscribes a pump chamber and includes a first sealing surface, an opposing second sealing surface, and a fluid transfer end interposed between the sealing surfaces. The support structure provides a fluid flow path running through the fluid transfer end and into the pump chamber via an inlet bore and from the pump chamber back through the fluid transfer end via an outlet bore. The first sealing element is disposed on the first sealing surface, and the second sealing element is disposed on the second sealing surface. The sealing elements are configured for forming sealing interfaces in the pump housing, establishing a static seal that isolates the pump chamber from an environment external to the fluid pump housing.

33 Claims, 13 Drawing Sheets

FLUID PUMPING VENTRICULAR ASSIST DEVICE AND COMPONENTS WITH STATIC SEAL

CROSS-REFERENCE TO RELATED APPLICATIONS

This application claims priority to U.S. Provisional App. Ser. No. 61/040,615, titled "Device For Hermetically Sealing A Ventricular Assist Device Chamber," filed on Mar. 28, 2008, which application is incorporated by reference in its entirety into this application.

TECHNICAL FIELD

The present invention generally relates to static seals and enclosures and devices utilizing static seals. As one particular example, the present invention relates to fluid pumping devices utilizing static seals such as ventricular assist devices.

BACKGROUND

In fluid pumping devices requiring the assembly of two or more components together, static seals may be utilized to prevent unwanted fluid leakage or flow at the interface between assembled components. Moreover, such fluid pumping devices may include internal regions that need to be maintained at a certain pressure or at least without the loss of pressure. Static seals may be utilized to prevent fluid leakage and pressure loss. Fluid pumping devices utilizing static seals include Ventricular Assist Devices (VADs), which are utilized as circulatory support devices for patients during or after open heart surgery or as a bridge to heart transplant for cardiac-failure patients. Other circulatory support devices include rotary blood pumps and axial blood pumps.

Typically, circulatory support devices include some type of a pumping unit, or components configured to provide a pumping action, contained in a suitable enclosure. The pumping unit of the circulatory support device may be connected to a patient's heart via cannulae attached to the heart at appropriate locations according to known surgical practices. Particularly in the case of a VAD, the pumping unit may include a flexible blood sac for supporting or replacing heart activity. The blood sac may be attached to an input cannula via a one-way input valve and to an output cannula via a one-way output valve. The enclosure for the blood sac may be provided in the form of two half shells that are coupled together to enclose the blood sac, resulting in an assembled VAD. A sealing element is included at the interface of the two half shells to hermetically seal the interior (containing the blood sac) from the environment external to the assembled VAD. The sealing element is typically constructed from a deformable material, while the half shells are rigid. Upon coupling the half shells together with the deformable sealing element therebetween, the half shells exert pressure on the sealing element. Consequently, the sealing element is compressed and essentially fills in (or conforms to) the interface between the half shells, thereby establishing a static seal. In the case where a flexible blood sac is employed as the pumping unit, one of the half shells may provide a fitting configured for connection to a pneumatic drive unit. The pneumatic drive unit may be operated to provide air or other gas to the interior of the enclosure in pulses (or fluctuating levels of pressure). In response to a pulse of air input, the blood sac is compressed (e.g., collapses, contracts, etc.), thereby pumping blood residing within the blood sac through the output cannula. Between pulses, the blood sac relaxes or expands to enable blood to fill the blood sac from the input cannula.

FIG. 1 is an exploded perspective view of a VAD 100 as described in U.S. Pat. No. 7,217,236, commonly assigned to the assignee of the present disclosure and incorporated herein by reference in its entirety into this application. The VAD 100 includes a disposable pumping unit 120 housed within a reusable pump shell 112. The pumping unit 120 includes a disposable blood sac 122 having an inlet 132 and outlet 134 respectively attached to a disposable one-way inlet valve 126 and outlet valve 124. Tubing connectors 130 and 128 are respectively attached to the inlet valve 126 and outlet valve 124 as interfaces to cannulae (not shown). The pump shell 112 includes an upper clamshell half 114 and a lower clamshell half 116. When assembled together, the upper clamshell half 114 and the lower clamshell half 116 define a pump chamber 142 in which the blood sac 122 resides. The lower clamshell half 116 has an air inlet 138 for connection to a pneumatic drive unit (not shown). The pneumatic drive unit provides a pulsed flow of air to the pump chamber 142 via the air inlet 138, thereby alternating the air pressure in the pump chamber 142 between high and low levels. In response, the blood sac 122 alternately contracts and expands such that blood is pumped along a flow path from the input tubing connector 130, to the inlet valve 126, the interior of the blood sac 122, the outlet valve 124, and to the output tubing connector 128.

In the VAD 100 illustrated in FIG. 1, a static, hermetic seal is formed at least in part by a disposable sealing element 118. The sealing element 118 is located along the plane of the interface between the upper clamshell half 114 and the lower clamshell half 116. Stated in another way, the sealing element 118 is located at the assembly plane of the two-piece pump shell 112 where the respective assembly faces of the upper clamshell half 114 and the lower clamshell half 116 meet. The configuration of the VAD 100, however, makes the ability of this sealing element 118 to consistently provide a hermetic seal at the assembly plane without pressure loss challenging. The configuration of the VAD 100 is characterized by the inlet and outlet fluidic lines being located on the same assembly plane as the faces of the upper clamshell half 114 and the lower clamshell half 116. Thus, as shown in FIG. 1, the inlet 132 and outlet 134 of the blood sac 122, the inlet valve 126 and the outlet valve 124, the tubing connectors 130 and 128, and the input and output cannulae (not shown) are all positioned essentially at the assembly plane between the upper clamshell half 114 and the lower clamshell half 116. Moreover, the tubing connectors 130 and 132 are located proximate to each other on the same side of the VAD 100.

Generally, this configuration for the VAD 100 may be considered as optimal for a variety of reasons. For instance, a surgeon can easily visualize and remember which tubing connectors 130 and 132 are being utilized for the input and output directions of blood flow, respectively. If the cannulae are initially connected to the wrong tubing connectors 130 and 132, the surgeon can easily switch the connections. Moreover, the inputs and outputs to the device are easily observable in one location to determine whether the blood sac 122 or one of the valves 124 and 126 has failed. In addition, assembly and disassembly of the VAD 100 for the purpose of replacing the blood sac 122 or the valves 124 and 126 is thought to be facilitated by this configuration. Ease of assembly and disassembly is particularly important during surgery. However, the configuration illustrated in FIG. 1 requires complex geometry, particularly with regard to various surfaces within the interior of the VAD 100. The valves 124 and 126 and tubing connectors 128 and 130 are accommodated by a cylindrical inlet region 146, a cylindrical outlet region 144, and associated grooves, surfaces, edges, and the like. The pump chamber 142 to be hermetically sealed is in open communication with the inlet region 146 and the outlet region 144. The location of the inlet region 146 and the outlet region 144 are such that there are essentially breaks in the assembly plane of the VAD 100. The sealing element 118 cannot adequately seal the inlet region 146 and the outlet region 144. Thus, hermetic sealing of the interior of the VAD 100 relies in part on securing the tubing connectors 128 and 130 to the upper clamshell half 114 and lower clamshell half 116 at locations such as annular shoulders 137 and the like.

In addition, the configuration illustrated in FIG. 1 requires that the assembly faces of the upper clamshell half 114 and lower clamshell half 116 be parallel to ensure pressure is imparted to the sealing element 118 uniformly. This parallelism limits the range of design options for the VAD 100 and results in the VAD 100 being larger and bulkier than necessary, which is particularly disadvantageous when the VAD 100 is intended to be implantable in the patient.

In addition, the blood sac 122, valves 124 and 126 and the cannulae connected to the valves 124 and 126 via the tubing connectors 130 and 132 are all constructed from a flexible material such as silicone rubber. Hence, these components are unstable during the handling and manipulation required for assembling the components together prior to enclosing them between the upper and lower clamshell halves 114 and 116. Once filled with fluid, these components are easy to deform, making proper handling and manipulation even more difficult.

Therefore, there is a need for providing a fluid pumping device that provides an improved static seal. There is also a need for providing a fluid pumping device that does not require parallel assembly faces and that is easier to assemble and disassemble. Further, there is a need for improving the stability of a fluid pumping device during assembly and disassembly.

SUMMARY

To address the foregoing problems, in whole or in part, and/or other problems that may have been observed by persons skilled in the art, the present disclosure provides methods, processes, systems, apparatus, instruments, and/or devices, as described by way of example in the various implementations set forth below.

According to one implementation, a static seal structure for a fluid pump housing includes a support structure, a first sealing element, and a second sealing element. The support structure circumscribes a pump chamber. The support structure includes a first sealing side, a second sealing side opposite to the first sealing side, a first opening located at the first sealing side, a second opening located at the second sealing side, a first sealing surface circumscribing the first opening, a second sealing surface circumscribing the second opening, a fluid transfer end interposed between the first sealing side and the second sealing side, a fluid inlet bore formed through the fluid transfer end, and a fluid outlet bore formed through the fluid transfer end. The support structure provides a fluid flow path running through the fluid transfer end and into the pump chamber via the fluid inlet bore and from the pump chamber back through the fluid transfer end via the fluid outlet bore. The first sealing element is disposed on the first sealing surface, and the second sealing element is disposed on the second sealing surface. The first sealing element and the second sealing element are configured for forming sealed interfaces between the support structure and the fluid pump housing when assembled in the fluid pump housing.

According to another implementation, a fluid pump housing includes a support structure, a first sealing element, a second sealing element, a first housing section and a second housing section. The support structure circumscribes a pump chamber. The support structure includes a first sealing side, a second sealing side opposite to the first sealing side, a first opening located at the first sealing side, a second opening located at the second sealing side, a first sealing surface circumscribing the first opening, a second sealing surface circumscribing the second opening, a fluid transfer end interposed between the first sealing side and the second sealing side, a fluid inlet bore formed through the fluid transfer end, and a fluid outlet bore formed through the fluid transfer end. The support structure provides a fluid flow path running through the fluid transfer end and into the pump chamber via the fluid inlet bore and from the pump chamber back through the fluid transfer end via the fluid outlet bore. The first sealing element is disposed on the first sealing surface, and the second sealing element is disposed on the second sealing surface. The first housing section contacts the first sealing element and covers the first opening, and the second housing section contacts the second sealing element and covers the second opening. The support structure, the first sealing element, the second sealing element, the first housing section, and the second housing section cooperatively fluidly seal the pump chamber from an environment external to the fluid pump housing, with the first sealing element forming a sealed interface between the first housing section and the support structure and the second sealing element forming a sealed interface between the second housing section and the support structure.

According to another implementation, a fluid pump includes a support structure, a first sealing element, a second sealing element, a first housing section, a second housing section, and a pump unit. The support structure circumscribes a pump chamber. The support structure includes a first sealing side, a second sealing side opposite to the first sealing side, a first opening located at the first sealing side, a second opening located at the second sealing side, a first sealing surface circumscribing the first opening, a second sealing surface circumscribing the second opening, a fluid transfer end interposed between the first sealing side and the second sealing side, a fluid inlet bore formed through the fluid transfer end, and a fluid outlet bore formed through the fluid transfer end. The first sealing element is disposed on the first sealing surface, and the second sealing element is disposed on the second sealing surface. The first housing section contacts the first sealing element and covers the first opening, and the second housing section contacts the second sealing element and covers the second opening. The pump unit is disposed in the pump chamber, and includes a pump inlet fluidly communicating with the fluid inlet bore and a pump outlet fluidly communicating with the fluid outlet bore. The support structure, the first sealing element, the second sealing element, the first housing section, and the second housing section cooperatively fluidly seal the pump chamber and the pump unit from an environment external to the fluid pump housing, with the first sealing element forming a sealed interface between the first housing section and the support structure and the second sealing element forming a sealed interface between the second housing section and the support structure.

According to another implementation, a method is provided for forming a static seal in a fluid pump housing. A support structure is seated in a first housing section such that a first sealing element is interposed between a first sealing surface of the support structure and a first inside surface of the first housing section. The support structure circumscribes a pump chamber and the first sealing element circumscribes a first opening between the interior space and a first interior of the first housing section. A second housing section is seated on the support structure such that a second sealing element is interposed between a second sealing surface of the support structure and a second inside surface of the second housing section. The second sealing surface is located on a side of the support structure opposite to the first sealing surface and circumscribes a second opening between the interior space and a second interior of the second housing section. The support structure, the first sealing element, the second sealing element, the first housing section, and the second housing section cooperatively fluidly seal the pump chamber from an environment external to the fluid pump housing.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 2:
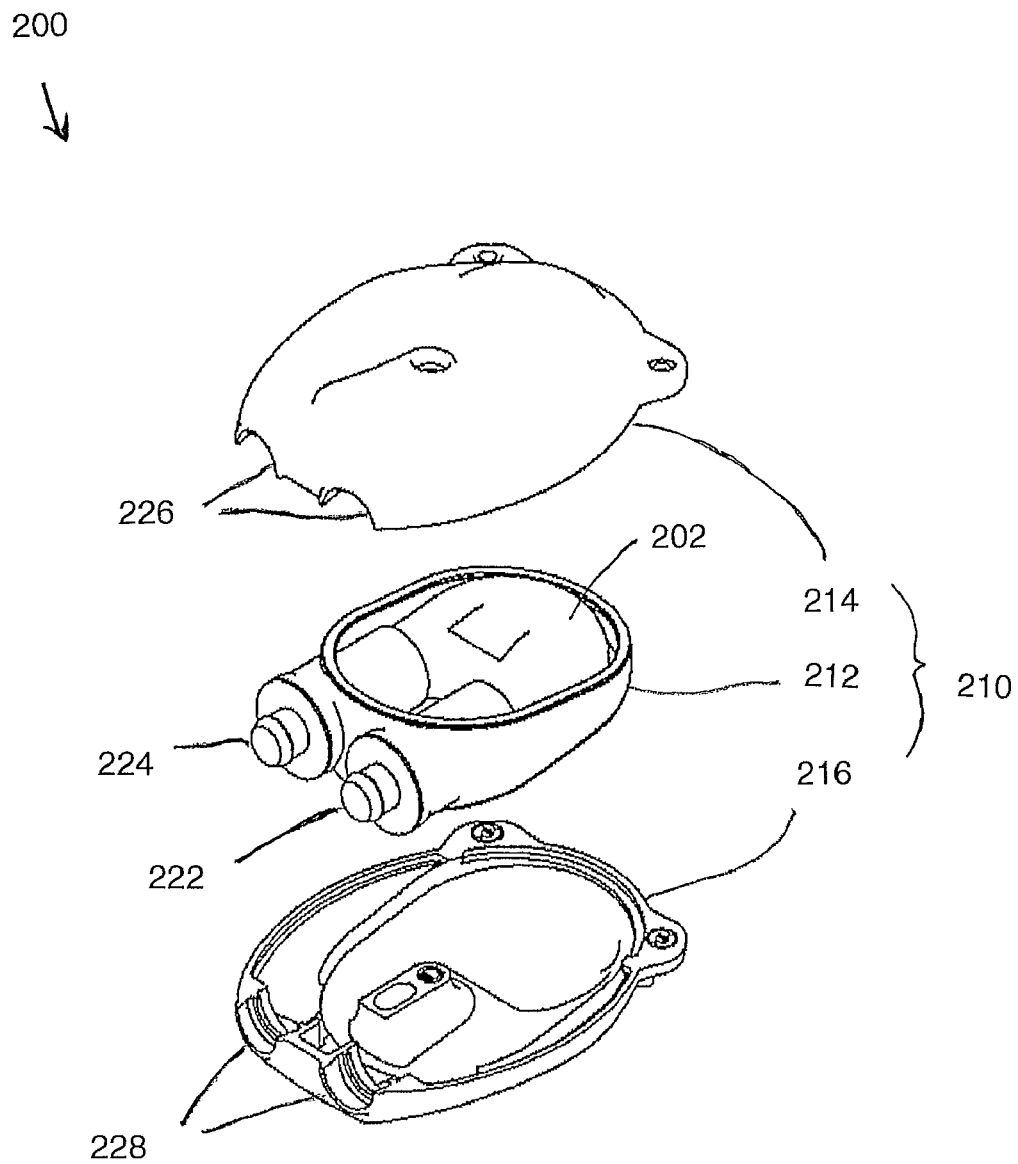
FIG. 2 is an exploded perspective view of an example of a fluid pump provided in accordance with the present invention.

FIG. 2 is an exploded perspective view of an example of a fluid pump 200 provided in accordance with the present invention. In the illustrated example, the pump 200 is adapted for use as a Ventricular Assist Device (VAD). As will become evident from the following description, however, the pump 200 is not limited to use as a VAD but rather may be utilized as another type of implantable or non-implantable pump. Moreover, the pump 200 may be adapted for use in non-medical as well as medical purposes. The pump 200 generally includes a pump unit 202 and a pump housing 210 that when assembled encloses and hermetically seals the pump unit 202. The pump unit 202 generally may be any device adapted to admit a volume of fluid into its interior through a pump inlet and discharge the fluid through a pump outlet via a pumping action. The fluid may be a liquid, gas, slurry, suspension, or the like. In the present example of a VAD, the pump unit 202 may be flexible sac adapted for pumping blood. The housing 210 includes a rigid support structure 212 surrounding the pump unit 202, a first housing section 214, and a second housing section 216. The support structure 212 and housing sections 214 and 216 may be constructed from any suitable rigid material such as various types of plastics, and may be fabricated by any suitable molding or machining process.

In assembling the pump 200, the pump unit 202 is placed in the support structure 212 in fluid communication with an inlet tubing connector 222 and an outlet tubing connector 224. The tubing connectors 222 and 224 may be constructed from any suitable rigid material such as various types of plastics and metals (e.g., stainless steel, titanium, etc.). The designation of one particular tubing connector 222 or 224 as being an inlet and the other tubing connector 224 or 222 as being an outlet is arbitrary and given merely by example. The support structure 212 is then placed in sealing contact with the first housing section 214 and the second housing section 216 in a manner described below. The first housing section 214 and the second housing section 216 are then secured together by fasteners or any other suitable means, resulting in a fully hermetically sealed pump 200. The tubing connectors 222 and 224 are secured directly to the support structure 212 and independently of the first housing section 214 and the second housing section 216. The first housing section 214 and the second housing section 216 may include respective surfaces 226 and 228 that form apertures after assembly to provide access to the tubing connectors 222 and 224. Neither the pump unit 202 nor the tubing connectors 222 and 224 need to be sealed to these apertures to maintain a static seal.

Figure 3:
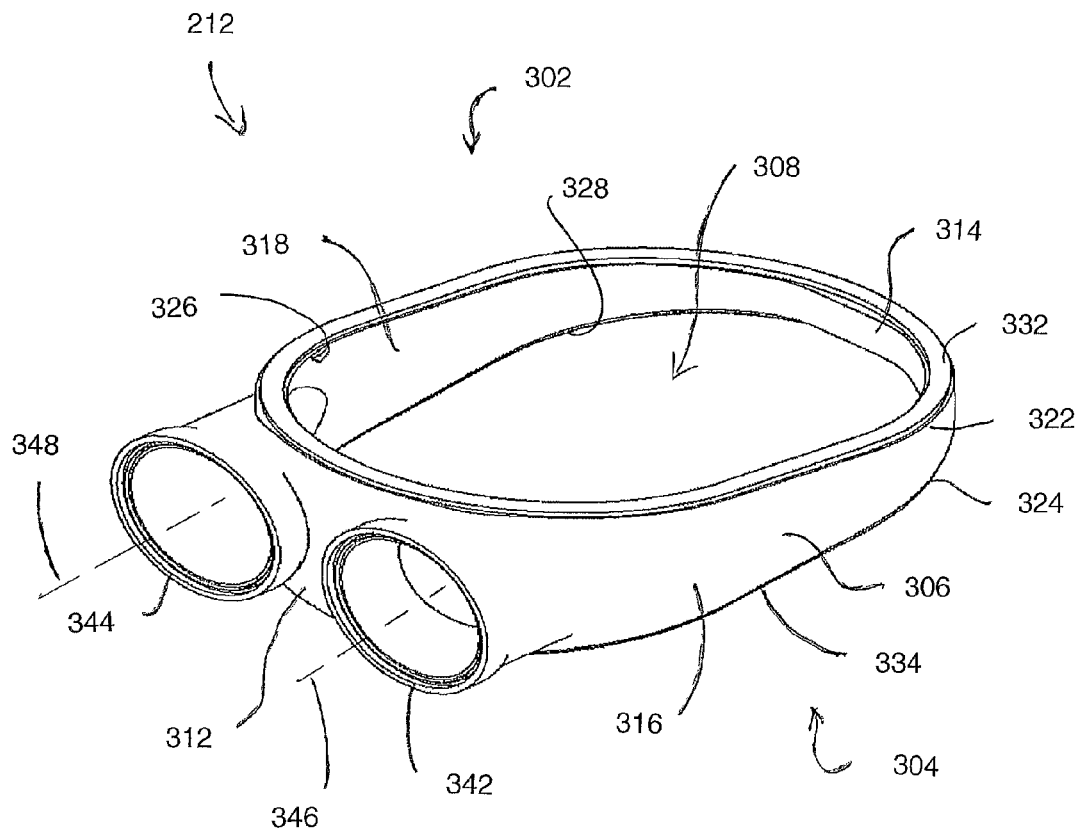
FIG. 3 is a perspective view of an example of a static seal structure that may be provided with the fluid pump illustrated in FIG. 2.
Figure 4:
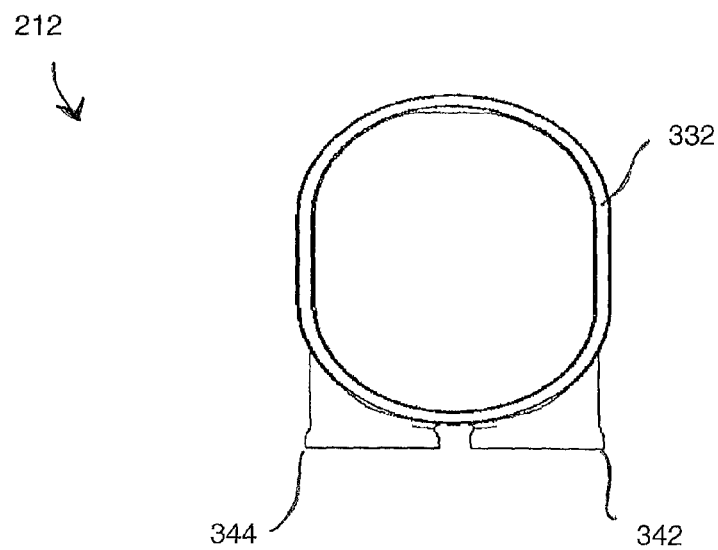
FIG. 4 is a plan view from a sealing side of the support structure illustrated in FIG. 3.
Figure 5:
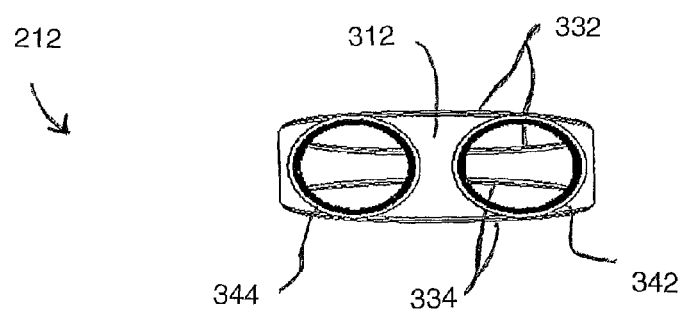
FIG. 5 is an elevation view from one end of the support structure illustrated in FIG. 3.
Figure 6:
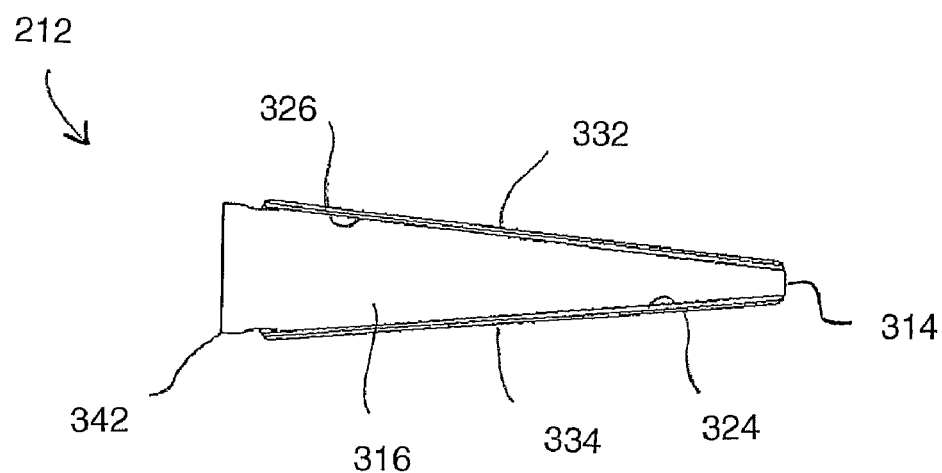
FIG. 6 is an elevation view from a lateral side of the support structure illustrated in FIG. 3.

FIGS. 3-6 illustrate the support structure 212 utilized to form a static seal for a pump such as the pump 200 illustrated in FIG. 2. Specifically, FIG. 3 is a perspective view, FIG. 4 is a plan view from a sealing side, FIG. 5 is an elevation view from one end, and FIG. 6 is a lateral side view.

Referring to FIG. 3, the support structure generally includes a first sealing side 302, an opposing second sealing side 304, and a wall 306 between the first sealing side 302 and second sealing side 304. In the present context, the wall 306 may include a single, continuous wall, or more than one wall where adjacent walls are adjoined. In either case, the wall 306 circumscribes an interior space 308 sized to receive the pump unit 202 (FIG. 2) and in part defining a sealed chamber of the pump 200. The support structure 212 generally includes a fluid transfer end 312, an end 314 opposite to the fluid transfer end 312, and opposing lateral sides 316 and 318 extending between the fluid transfer end 312 and the opposing end 314. The support structure 212 also includes a first sealing surface 322 at the first sealing side 302 and an opposing second sealing surface 324 at the second sealing side 304. The first sealing surface 322 circumscribes a first opening 326 and the second sealing surface 324 circumscribes a second opening 328. Each sealing surface 322 and 324 may have a flat or rounded profile and may or may not be provided in the form of a groove. More generally, the first sealing surface 322 is configured to receive a first sealing element 332 and the second sealing surface 324 is configured to receive a second sealing element 334. The sealing elements 332 and 334 may be constructed of any suitable deformable or elastic material. The sealing elements 332 and 334 may be structured as continuous loops of material. In the present example, the sealing elements 332 and 334 include curved sections at the fluid transfer end 312 and opposing end 314 and straight sections along the lateral sides 316 and 318. The sealing elements 332 and 334 together with the support structure 212 form a static seal structure.

In one implementation, the support structure 212 and sealing elements 332 and 334 form a multi-piece static seal structure. In this implementation, the sealing elements 332 and 334 are initially physically separate components that are first placed in properly aligned or oriented contact with either the respective sealing surfaces 322 and 324 or the corresponding inside surfaces of the housing sections 214 and 216 prior to assembling the support structure 212 and housing sections 214 and 216 securely together. In another implementation, the support structure 212 and sealing elements 332 and 334 are initially provided as a one-piece static seal structure prior to assembly with the housing sections 214 and 216. In this implementation, the sealing elements 332 and 334 are initially affixed to the respective sealing surfaces 322 and 324 by any suitable means. As one non-limiting example, the support structure 212 and sealing elements 332 and 334 may all be fabricated together in situ in a double injection manufacturing process. As appreciated by persons skilled in the art, the double injection manufacturing process enables dissimilar polymers or different polymeric components to be joined together. In other implementations, the sealing elements 332 and 334 may be bonded or adhered to the respective sealing surfaces 322 and 324 by any other suitable means that does not impair the deformability or elasticity of the sealing elements 332 and 334.

Continuing with FIG. 3, an inlet bore 342 and an outlet bore 344 are both formed at the fluid transfer end 312 of the support structure 212 in open communication with the interior space 308. The designation of one of these bores 342 or 344 as being the inlet and the other bore 344 or 342 as being the outlet is arbitrary and given merely by example. The inlet bore 342 is oriented about an inlet axis 346 along which fluid flows through the fluid transfer end 312 into the pump unit 202 (FIG. 2). The outlet bore 344 is oriented about an outlet axis 348 along which fluid flows from the pump unit 202 and back through the fluid transfer end 312. The inlet bore 342 and the outlet bore 344 may be configured and positioned such that the inlet axis 346 and the outlet axis 348 are parallel to each other and lie in the same plane, as in the illustrated example. In other implementations, the inlet axis 346 and the outlet axis 348 may be non-parallel. As also shown in FIG. 3, the inlet bore 342 and the outlet bore 344 may be sized to receive tubing connectors 222 and 224 (FIG. 2) of a standard size. The portion of the wall 306 associated with the fluid transfer end 312 is tall enough to accommodate the inlet bore 342 and the outlet bore 344. However, as shown in FIG. 3 and further in FIG. 6, the first sealing element 332 and the second sealing element 334 may be non-parallel in accordance with certain implementations of the present invention. In this case, the wall 306 of the support structure 212 along the lateral sides 316 and 318 may taper from the height at the fluid transfer end 312 down to a lesser height at the opposite end 314.

Figure 7:
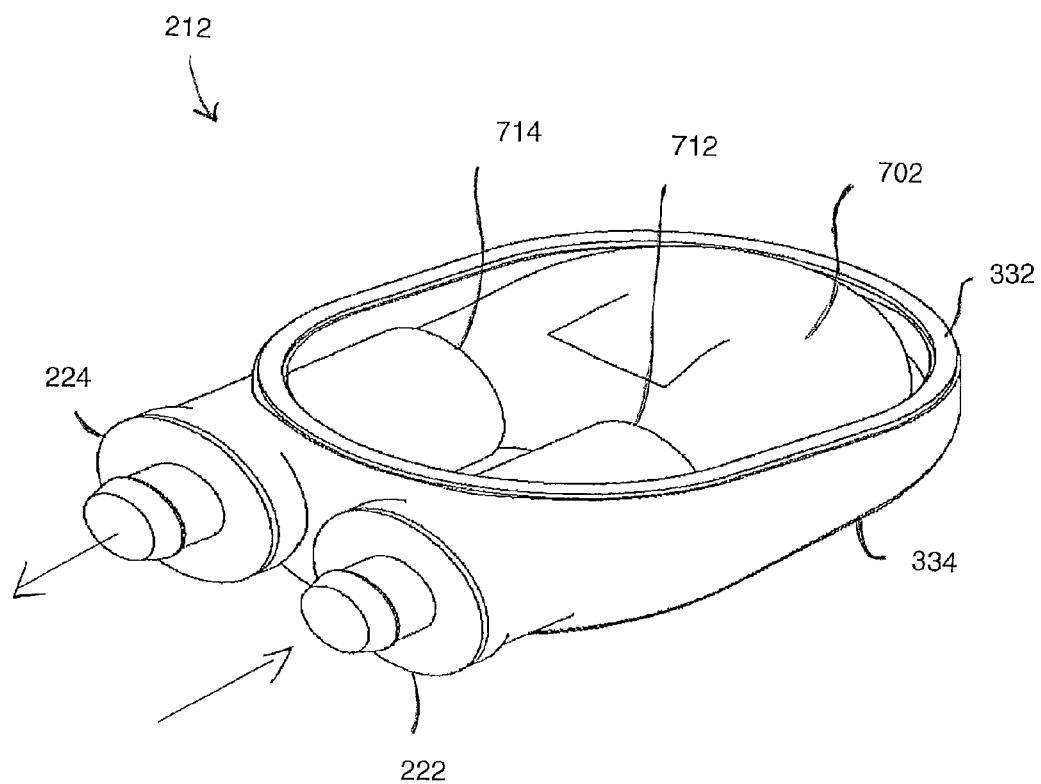
FIG. 7 is a perspective view of an example of a pump unit of the fluid pump illustrated in FIG. 2 installed with the support structure illustrated in FIG. 3.
Figure 8:
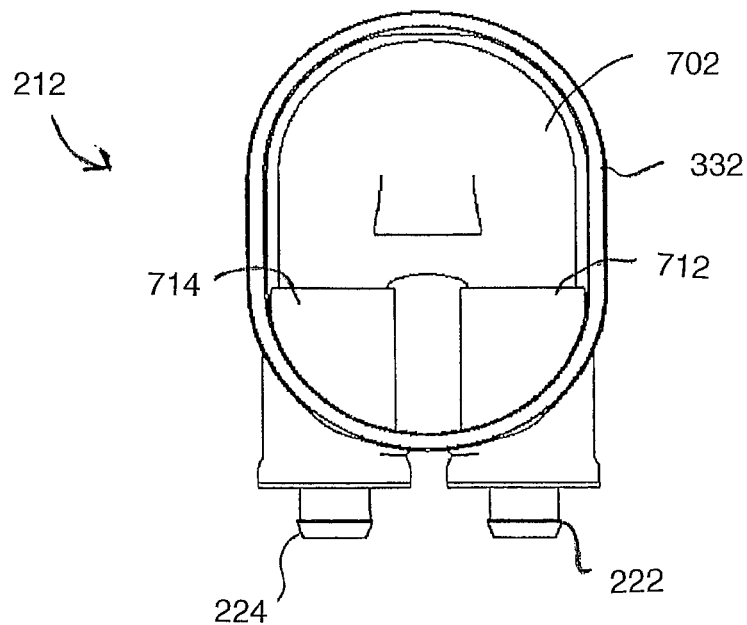
FIG. 8 is a plan view from a sealing side of the pump unit and support structure illustrated in FIG. 7.
Figure 9:
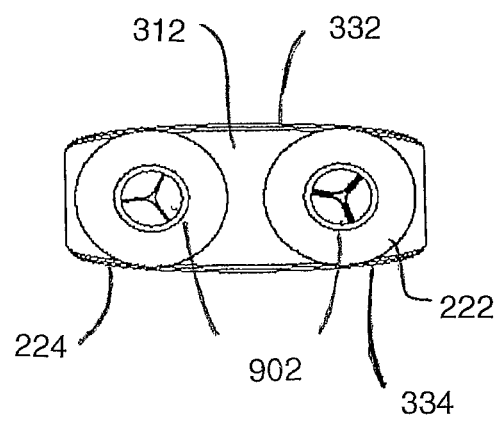
FIG. 9 is an elevation view from a fluid transfer end of the pump unit and support structure illustrated in FIG. 7.
Figure 10:
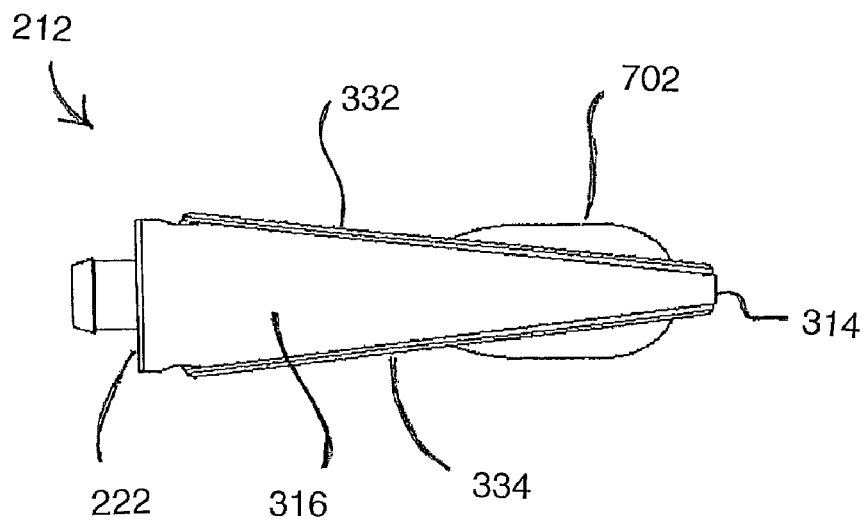
FIG. 10 is a lateral side of the pump unit and support structure illustrated in FIG. 7.

FIGS. 7-10 illustrate the pump unit 202 installed with the support structure 212. Specifically, FIG. 7 is a perspective view, FIG. 8 is a plan view from a sealing side, FIG. 9 is an elevation view from the fluid transfer end, and FIG. 10 is an elevation view from a lateral side.

Figure 1:
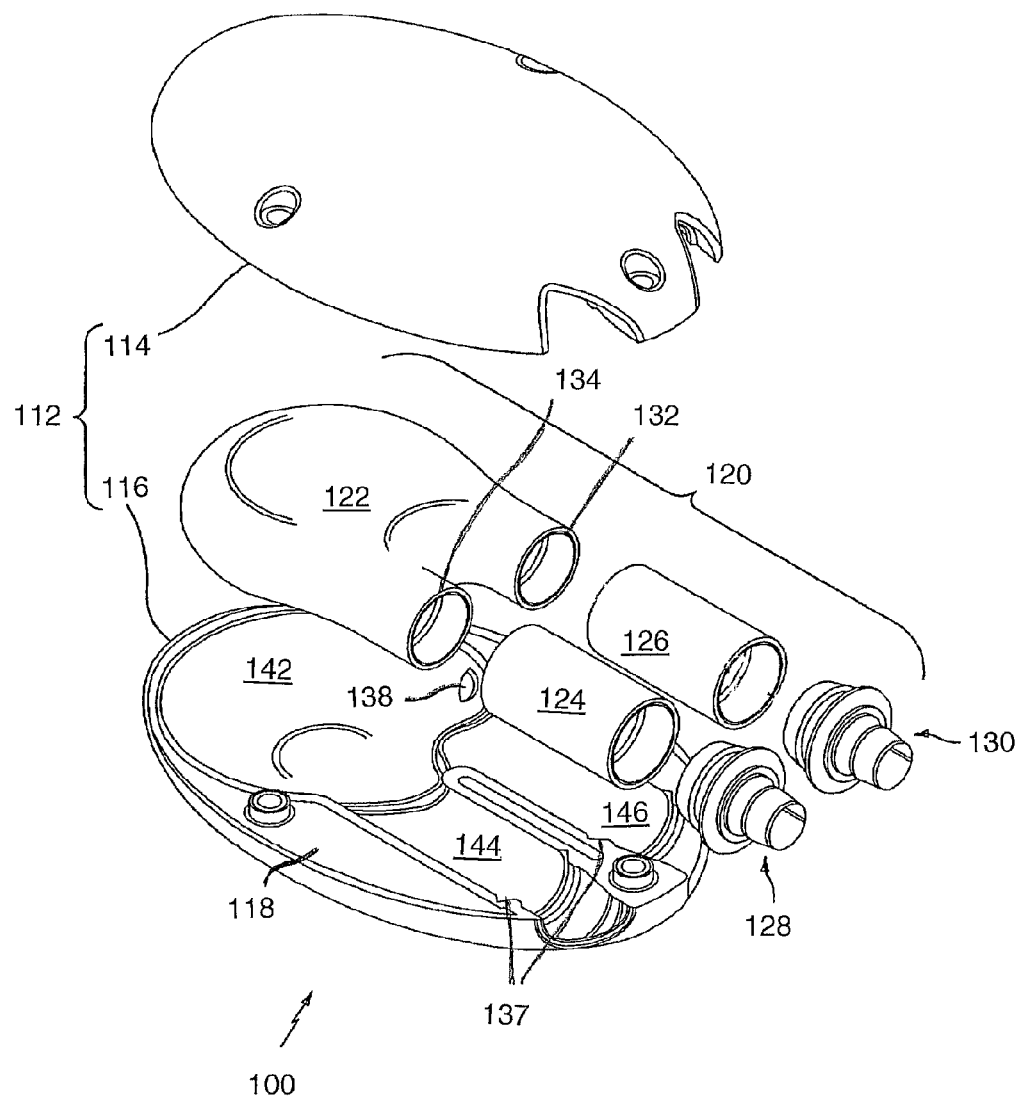
FIG. 1 is an exploded perspective view of a known Ventricular Assist Device (VAD).

Referring to FIG. 7, the pump unit 202 generally includes a structural enclosure 702 enclosing a pump interior in fluid communication with a pump inlet and a pump outlet. The specific configuration of the pump unit 202 may depend on the particular application of the pump 200 and the type of fluid to be pumped. In the present example of a VAD, at least a portion of the enclosure 702 of the pump unit 202 is flexible such that the internal volume of the pump unit 202 varies between contraction/expansion cycles of the enclosure 702. Accordingly, the pump unit 202 may be configured similarly to the flexible blood sac described above in conjunction with FIG. 1. All or a portion of the pump unit 202 may be constructed from a supple elastomer such as silicone, and the pump unit 202 may have a generally rounded profile with no sharp or abrupt edges. Such a configuration is suitable for preventing damage to blood tissue during pumping. A one-way inlet valve 712 is connected to the inlet of the pump unit 202, and a one-way outlet valve 714 is connected to the outlet of the pump unit 202. The inlet valve 712 and the outlet valve 714 thus fluidly communicate with the pump interior but are detachable from the pump inlet and pump outlet for replacement, cleaning, or the like. The interior space 308 (FIG. 3) defined by the support structure 212 is large enough to accommodate the inlet valve 712 and the outlet valve 714. The ends of the inlet valve 712 and outlet valve 714 opposite to the pump unit 202 are attached to the respective tubing connectors 222 and 224. The inlet valve 712 and outlet valve 714 may be coupled to the pump unit 202 and tubing connectors 222 and 224 by any suitable means such as, for example, friction fit, threading, Luer-type fitting, etc.

The tubing connectors 222 and 224 may be securely mounted to the inlet bore 342 and outlet bore 344 (FIG. 3) in any suitable sealed manner that prevents fluid leakage from the interior space 308 through the inlet bore 342 and outlet bore 344. In one example, the tubing connectors 222 and 224 may include threads that mate with complementary threads formed on the inside surface of the inlet bore 342 and outlet bore 344. Because the inlet bore 342 and outlet bore 344 are formed through the one-piece support structure 212, instead of by assembly of two housing sections together, the tubing connectors 222 and 224 are easily sealed against the inlet bore 342 and outlet bore 344 without risk of leakage.

When the various components are assembled as illustrated in FIG. 7, a fluid flow path is established in which fluid enters the input tubing connector 222 as indicated by an arrow, passes through the fluid transfer end 312 of the support structure 212, flows through the inlet valve 712 and into the interior of the pump unit 202, flows out from the pump interior and through the outlet valve 714, passes back through the fluid transfer end 312, and exits the output tubing connector 224 as indicated by an arrow. In practice, an input conduit (not shown) may be connected between the input tubing connector 222 and a suitable fluid source, and an output conduit (not shown) may be connected between the output tubing connector 224 and a suitable fluid destination. In the case of a VAD, the input and output conduits may be medical-grade cannulae attached to a patient's heart according to known surgical procedures.

Various components of the pump 200, such as for example the pump unit 202, valves 712 and 714, cannulae, etc. may be fabricated or treated for specific purposes such as to improve blood compatibility and non-thrombogenicity. As examples, such components may be coated with lubricant, hydrophobic, antibacterial and/or antithrombotic coatings, including but not limited to PTFE coatings, heparin-bonded coatings, fluorinated coatings, treclosan and silver compound coatings, anti-calcification agent-releasing coatings, etc.

Referring to FIGS. 2, 7 and 8, it can be seen that the interior chamber of the pump 200, which includes the interior space 308 (FIG. 3) circumscribed by the support structure 212, is completed upon assembly of the first housing section 214 to the second housing section 216 with the support structure 212 interposed between these two housing sections 214 and 216. During assembly, the first sealing element 332 is properly seated against a complementary interior surface of the first housing section 214, and the second sealing element 334 is properly seated against a complementary interior surface of the second housing section 216. Compression and consequent deformation of the first and second sealing elements 332 and 334 between the support structure 212 and the respective first and second housing sections 214 and 216 results in the interior chamber of the pump 200 being hermetically sealed. The components associated with the inlet and outlet fluidic lines (e.g., the inlet and outlet of the pumping unit 202, the inlet and outlet valves 712 and 714, the inlet and outlet bores 342 and 344 of the support structure, and the tubing connectors 222 and 224) are still located in a position considered advantageous in many implementations, including applications entailing ventricular assistance, i.e., in between two housing sections 214 and 216 that are assembled together to enclose a pump unit 202. Due to the illustrated configuration, however, these components do not break or interfere with the assembly planes associated with the housing sections 214 and 216. In particular, the tubing connectors 222 and 224 are remote from and completely independent of the first and second sealing elements 332 and 334 that serve as the assembly interfaces of the structural components of the pump housing 210. Moreover, as further shown in FIG. 10, the static seal established according to the present invention does not require sealing interfaces to be parallel.

FIG. 9 illustrates that the inlet valve 712 and outlet valve 714 may be configured as one-way valves, such as through the use of two or more flaps or leaflets 902 in each valve 712 and 714 configured for allowing fluid flow in a single direction. A further example of one-way valves is described below in conjunction with FIGS. 13 and 14.

FIG. 10 illustrates an implementation in which the support structure 212 is tapered such that the first sealing element 332 and second sealing element 334 are positioned in a non-parallel relation. In this case, the pump unit 202 may protrude out from the first sealing side 302 and the second sealing side 304 of the support structure 212. The interior profiles of the first and second housing sections 214 and 216 (FIG. 2) may be configured to be just large enough to enclose the pump unit 202 and provide some space for a gas (e.g. air) to be admitted into the interior chamber of the pump 200 for activating the pumping action of the pump unit 202. Because the first sealing element 332 and second sealing element 334 are not required to be parallel, the pump housing 210 does not need to assume a more traditional cylindrical or box-like shape. Instead, the pump housing 210 can be made smaller and occupy less volume, which is particularly useful in implantable applications.

Figure 11:
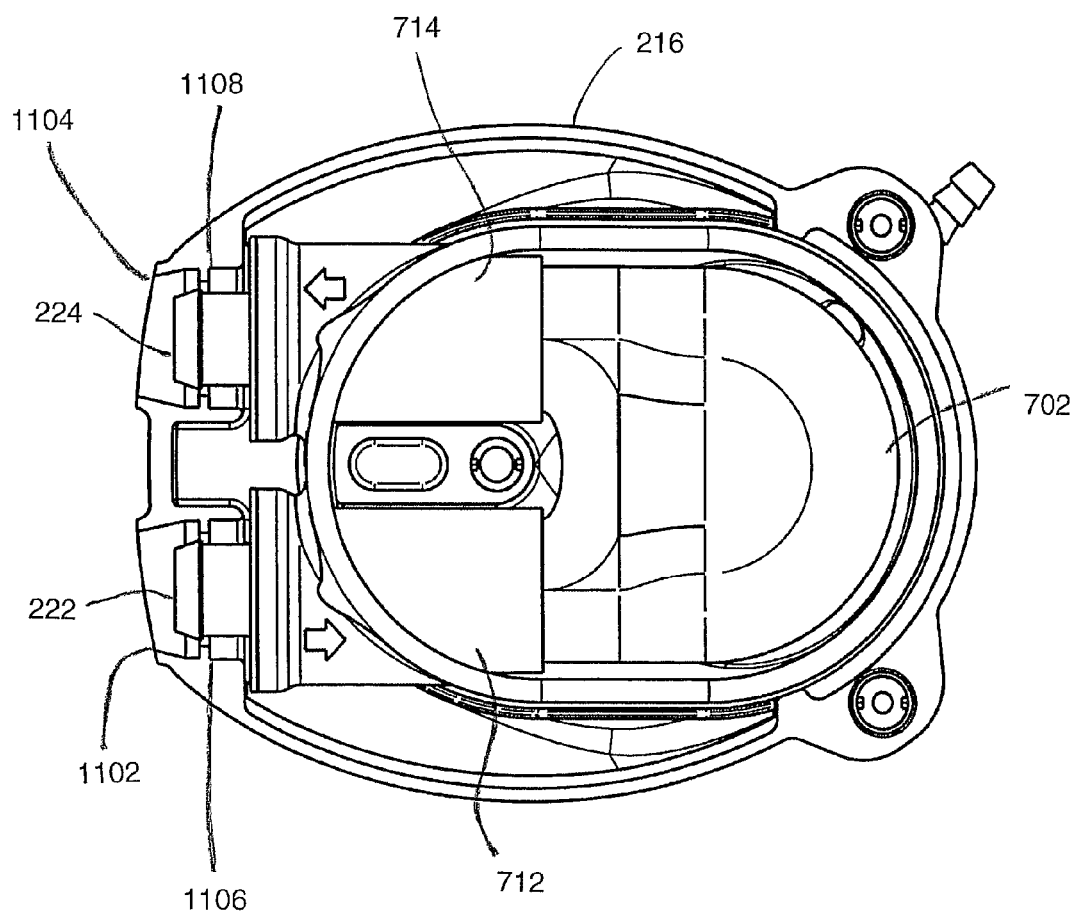
FIG. 11 is a plan view illustrating the pump unit and support structure seated in a housing section.

FIG. 11 is a plan view illustrating the pump unit 202 and support structure 212 seated in a housing section 214 (or 216). The housing sections 214 and 216 may provide openings 1102 and 1104 for accessing the tubing connectors 222 and 224, as well as features such as annular shoulders 1106 and 1108 for facilitating the connection of cannulae or other types of conduits to the tubing connectors 222 and 224. However, the tubing connectors 222 and 224 are not required to be sealingly coupled to these openings 1102 and 1104 to form a static seal. Instead, the tubing connectors 222 and 224 may be securely coupled to the inlet bore 342 and outlet bore 344 of the support structure 212, with the static seal being established by the sealing elements 332 and 334.

Figure 12:
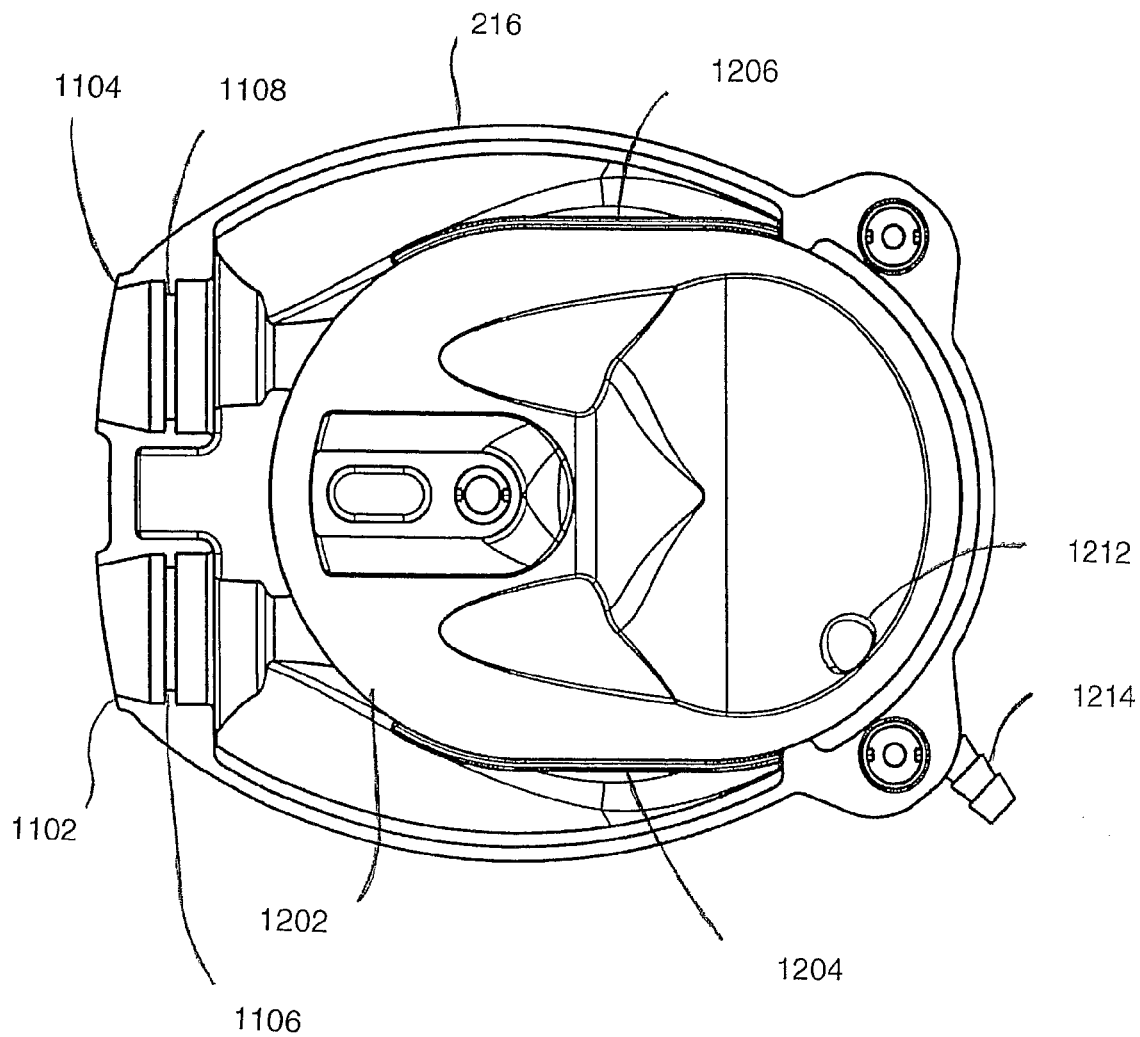
FIG. 12 is a plan view illustrating the same housing section as illustrated in FIG. 11 but with the pump unit and support structure removed.

FIG. 12 is a plan view illustrating the same housing section 214 (or 216) as illustrated in FIG. 11 but with the pump unit 202 and support structure 212 removed. Each housing section 214 and 216 may include an inside sealing surface 1202 configured for complete, uniform contact with the corresponding sealing element 332 or 334. The inside sealing surface 1202 may have a flat or rounded profile and may or may not be provided in the form of a groove. The inside sealing surface 1202 may be a continuous surface to ensure uniform contact with, and pressure imparted to, the sealing element 332 or 334. As also illustrated in FIG. 12, the housing sections 214 and 216 may include shoulders or ridges 1204 and 1206 proximate to their corresponding inside sealing surfaces 1202 to facilitate seating the rigid support structure 212 (FIG. 11) in an aligned manner that ensures the establishment of a proper sealing interface. As also shown in FIG. 12, at least one of the housing sections may include a gas (e.g., air) port 1212 and associated fitting 1214 for connection to a pneumatic drive unit (not shown). As described earlier, the pneumatic drive unit or equivalent device may be operated to inject a gas into the chamber of the pump 200 in a pulsed manner to activate the pumping action of the pump unit 202 (FIG. 11).

The pump 200 may be easily assembled and disassembled. As an example of assembling the pump 200, the tubing connectors 222 and 224 are secured to the respective inlet bore 342 and outlet bore 344 of the support structure 212. The inlet valve 712 and outlet valve 714 may then be connected to the respective inlet and outlet of the pump unit 202 and to the corresponding tubing connectors 222 and 224. The support structure 212 (with the associated components mounted thereto) may then be placed in contact with the appropriate inside surface 1202 of one of the housing sections 214 and 216, with one of the sealing elements 332 and 334 being interposed between the support structure 212 and the housing section 214 or 216. The other housing section 216 or 214 may then be brought into contact with the opposing sealing side of the support structure 212, with the other sealing element 334 or 332 being interposed between the support structure 212 and the housing section 216 or 214. The housing sections 214 and 216 are then secured or fastened together by any suitable means, thereby compressing the sealing elements 332 and 334 and establishing the fluid-tight, active static seal of the pump 200. Input and output cannulae (to other type of conduits) may be connected to the corresponding tubing connectors 222 and 224 before or after the housing sections 214 and 216 are secured to the support structure 212. In an implementation where one or both of the housing sections 214 and 216 include features adapted to enhance securement of the cannulae to the tubing connectors (e.g., shoulders, edges or the like for effecting a crimping, clamping or locking action), the cannulae may be connected to the tubing connectors 222 and 224 prior to securing the housing sections 214 and 216 to the support structure 212. It can also be seen that the support structure 212 provides a rigid component facilitating handling and manipulation of the various components during assembly and disassembly. The support structure 212 may be directly handled by the user when attaching/detaching the inlet valve 712 and outlet valve 714 to/from the pump unit 202 and tubing connectors 222 and 224, and attaching/detaching the tubing connectors 222 and 224 to/from cannulae.

Figure 13:
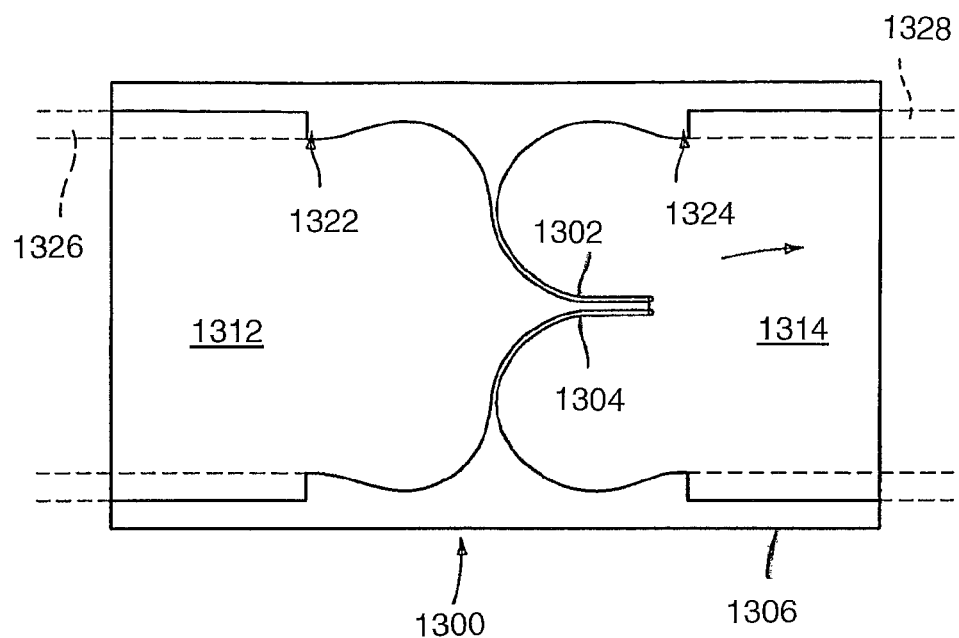
FIG. 13 is a cross-sectional elevation view of an example of a one-way valve that may be utilized in the fluid pump illustrated in FIG. 2.
Figure 14:
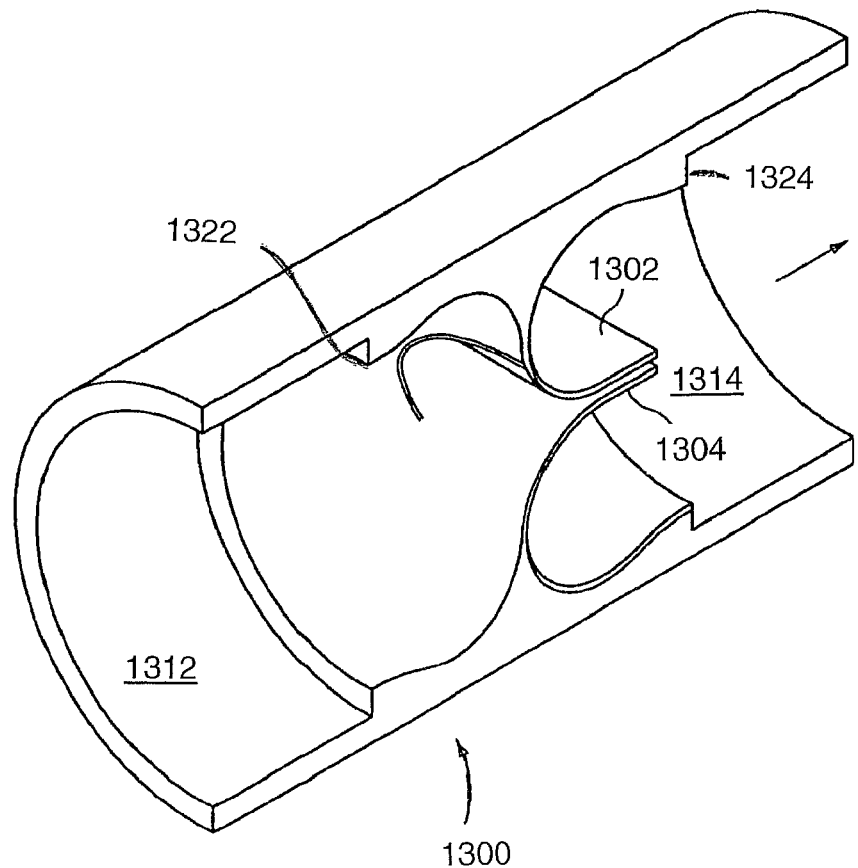
FIG. 14 is a cross-sectional perspective view of the one-way valve illustrated in FIG. 13.

FIG. 13 is a cross-sectional elevation view and FIG. 14 is a cross-sectional perspective view of an example of a one-way valve 1300 that may be utilized as the inlet and outlet valves described above. It will be understood, however, that various other configurations may be provided for the one-way valves utilized in the presently described implementations. In the present example, the one-way valve 1300 may have a hingeless design in which two or more flexible, elastic flaps or leaflets 1302 and 1304 extend generally toward each other from an inside surface of a main valve body 1306. The flaps 1302 and 1304 are positioned between an inlet end 1312 and an outlet end 1314 of the one-way valve 1300. The flaps 1302 and 1304 are shaped such that when the fluid pressure at the inlet end 1312 is greater than the fluid pressure at the outlet end 1314, the flaps 1302 and 1304 flex away from each other whereby fluid flows from the inlet end 1312 to the outlet end 1314. When the fluid pressure at the inlet end 1312 is less than the fluid pressure at the outlet end 1314, the flaps 1302 and 1304 are compressed together whereby fluid is prevented from flowing from the outlet end 1314 back toward the inlet end 1312. The one-way valve 1300 is configured such that the opening and closing of the flaps 1302 and 1304 is gentle and enables a smooth and continuous flow of fluid in the intended direction and in a manner similar to the action of a natural heart valve. The one-way valve 1300 may be configured without any sharp edges and the material may be a supple elastomer such as, for example, silicone. The one-way valve 1300 may be formed by injection molding or any other suitable method of fabrication. A one-way valve such as illustrated in FIGS. 13 and 14 minimizes or eliminates the risk of damage to blood cells and hence is suitable for flowing blood.

As further illustrated by example in FIG. 13, the one-way valve 1300 may include inside annular shoulders or surfaces 1322 and 1324 sized to abut the respective ends of an inlet conduit 1326 and an outlet conduit 1328. It will be appreciated, however, that alternative coupling configurations may be implemented. In a case where the one-way valve 1300 is utilized as an inlet valve, the inlet conduit 1326 may represent an inlet tubing connector and the outlet conduit 1328 may represent the inlet of a pump unit. In a case where the one-way valve 1300 is utilized as an outlet valve, the inlet conduit 1326 may represent the outlet of a pump unit and the outlet conduit 1328 may represent an outlet tubing connector.

Figure 15:
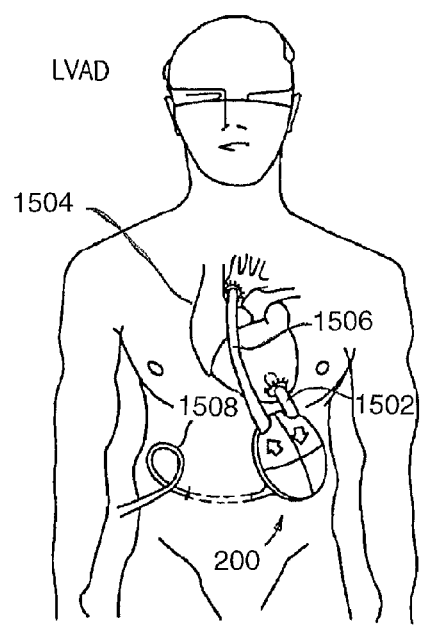
FIG. 15 illustrates an example of the use of the fluid pump as a Left Ventricular Assist Device (LVAD).
Figure 16:
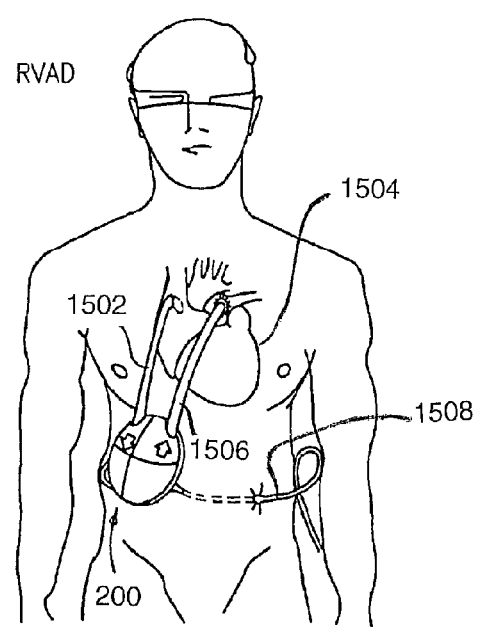
FIG. 16 illustrates an example of the use of the fluid pump as a Right Ventricular Assist Device (RVAD).
Figure 17:
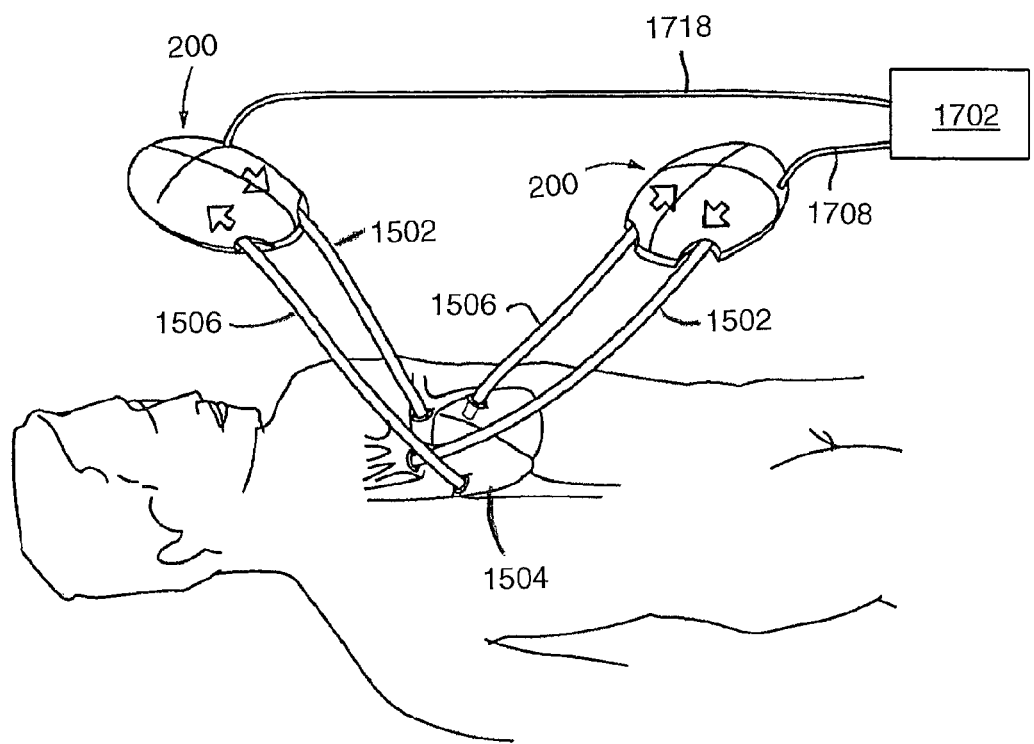
FIG. 17 illustrates an example of the use of two fluid pumps as a Bi-Ventricular Assist Device (BIVAD).

FIGS. 15-17 illustrate examples of applications of the pump 200 described above. FIG. 15 illustrates the use of the pump 200 as a Left Ventricular Assist Device (LVAD). A ventricular (or atrial) cannula 1502 is attached to the input tubing connector of the pump 200 and surgically attached to an appropriate site of a patient's heart 1504, thereby providing a flow path for blood from the heart 1504 into the pump 200. An arterial cannula 1506 is attached to the output tubing connector of the pump 200 and surgically attached to an appropriate site of the heart 1504, thereby providing a flow path for blood from the pump 200 into the heart 1504. A pneumatic line 1508 is interconnected between the pump 200 and a pneumatic drive device or equivalent gas (e.g., air) source 1702 (FIG. 17) to provide a pulsed flow of gas for actuating the pump 200 as described above. FIG. 16 illustrates the use of the pump 200 as a Right Ventricular Assist Device (RVAD). FIG. 17 illustrates the use of two pumps 200 as a Bi-Ventricular Assist Device (BIVAD). The two pumps 200 are driven by the pneumatic drive device 1702 via respective pneumatic lines 1708 and 1718.

FIGS. 15-17 illustrate examples of extracorporeal applications of the pump 200. It will be appreciated, however, that the pump 200 may be utilized in paracorporeal implementations and as a tethered implant. As noted above, the pump 200 is configured in accordance with the present invention such that its size may be reduced relative to pumps of conventional design, thereby greatly facilitating implantable implementations. The pump 200 may be utilized in a wide variety of circulatory supporting applications, including short-term trans-operative support (e.g., a few hours), acute and post-cardiotomy support (e.g., up to a few weeks), bridge to transplant (e.g., three to six months), bridge to recovery (e.g., several years), and destination therapy (i.e., until death). More generally, the pump 200 may be utilized in various non-medical as well as medical applications for pumping various types of fluids. In addition to the flexible-sac configuration described by example above, other types of pump units may benefit through the use of the static seal provided by the present invention.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A ventricular assist device (VAD) static seal structure for a fluid pump housing, comprising:

a support structure circumscribing a pump chamber, the support structure including a first sealing side, a second sealing side opposite to the first sealing side, a first opening located at the first sealing side, a second opening located at the second sealing side, a first sealing surface circumscribing the first opening, a second sealing surface circumscribing the second opening, a fluid transfer end interposed between the first sealing side and the second sealing side, a fluid inlet bore formed through the fluid transfer end, and a fluid outlet bore formed through the fluid transfer end, wherein the support structure provides a fluid flow path running through the fluid transfer end and into the pump chamber via the fluid inlet bore and from the pump chamber back through the fluid transfer end via the fluid outlet bore;

a first sealing element disposed on the first sealing surface; and a second sealing element disposed on the second sealing surface, wherein the first sealing element and the second sealing element are configured for forming sealed interfaces between the support structure and interior surfaces of the fluid pump housing when the support structure is fitted within the fluid pump housing.

2. The VAD static seal structure of claim 1, wherein the first sealing element is parallel to the second sealing element.

3. The VAD static seal structure of claim 1, wherein the first sealing element is non-parallel to the second sealing element.

4. The VAD static seal structure of claim 1, wherein the fluid inlet bore is disposed about an inlet axis, and the fluid outlet bore is disposed about an outlet axis parallel to the inlet axis.

5. The VAD static seal structure of claim 1, wherein the fluid inlet bore is disposed about an inlet axis, and the fluid outlet bore is disposed about an outlet axis non-parallel to the inlet axis.

6. The VAD static seal structure of claim 1, further including an inlet tubing connector attached to the fluid inlet bore, and an outlet tubing connector attached to the fluid outlet bore.

7. The VAD static seal structure of claim 1, wherein the first sealing element and the second sealing element are each configured as a continuous loop of material.

8. The VAD static seal structure of claim 1, wherein the first sealing surface and the second sealing surface are continuous surfaces.

9. A ventricular assist device (VAD) fluid pump housing, comprising:
a support structure circumscribing a pump chamber, the support structure including a first sealing side, a second sealing side opposite to the first sealing side, a first opening located at the first sealing side, a second opening located at the second sealing side, a first sealing surface circumscribing the first opening, a second sealing surface circumscribing the second opening, a fluid transfer end interposed between the first sealing side and the second sealing side, a fluid inlet bore formed through the fluid transfer end, and a fluid outlet bore formed through the fluid transfer end, wherein the support structure provides a fluid flow path running through the fluid transfer end and into the pump chamber via the fluid inlet bore and from the pump chamber back through the fluid transfer end via the fluid outlet bore;
a first sealing element disposed on the first sealing surface;
a second sealing element disposed on the second sealing surface;
a first housing section having an interior surface contacting the first sealing element and covering the first opening; and
a second housing section having an interior surface contacting the second sealing element and covering the second opening, the second housing section being secured to the first housing section to form a housing in which the support structure is fitted,
wherein the support structure, the first sealing element, the second sealing element, the first housing section, and the second housing section cooperatively fluidly seal the pump chamber from an environment external to the fluid pump housing, with the first sealing element forming a sealed interface between the first housing section and the support structure and the second sealing element forming a sealed interface between the second housing section and the support structure.

10. The VAD fluid pump housing of claim 9, wherein the first sealing element is parallel to the second sealing element.

11. The VAD fluid pump housing of claim 9, wherein the first sealing element is non-parallel to the second sealing element.

12. The VAD fluid pump housing of claim 9, wherein the fluid inlet bore is disposed about an inlet axis, and the fluid outlet bore is disposed about an outlet axis parallel to the inlet axis.

13. The VAD fluid pump housing of claim 9, wherein the fluid inlet bore is disposed about an inlet axis, and the fluid outlet bore is disposed about an outlet axis non-parallel to the inlet axis.

14. The VAD fluid pump housing of claim 9, further including an inlet tubing connector attached to the fluid inlet bore, and an outlet tubing connector attached to the fluid outlet bore.

15. The VAD fluid pump housing of claim 14, wherein the first housing section and the second housing section secured to the first housing section comprise openings for accessing the inlet tubing connector and the outlet tubing connector, the openings being formed in a side of the housing formed by the first and second housing sections that overlaps the fluid transfer end of the support structure.

16. The VAD fluid pump housing of claim 9, wherein the first sealing element and the second sealing element are each configured as a continuous loop of material.

17. The VAD fluid pump housing of claim 9, wherein the first sealing surface and the second sealing surface are continuous surfaces.

18. The VAD fluid pump housing of claim 9, wherein a gas inlet is formed in at least one of the first housing section and the second housing section, the gas inlet fluidly communicating with the pump chamber and configured for connection to a gas conduit.

19. The VAD fluid pump housing of claim 9, wherein the first housing section and the second housing section comprise ridges proximate to their corresponding first and second sealing surface to facilitate sealing the support structure in an aligned manner.

20. A ventricular assist device (VAD) fluid pump, comprising:
a rigid support structure circumscribing a pump chamber, the support structure including a first sealing side, a second sealing side opposite to the first sealing side, a first opening located at the first sealing side, a second opening located at the second sealing side, a first sealing surface circumscribing the first opening, a second sealing surface circumscribing the second opening, a fluid transfer end interposed between the first sealing side and the second sealing side, a fluid inlet bore formed through the fluid transfer end, and a fluid outlet bore formed through the fluid transfer end;
a first sealing element disposed on the first sealing surface;
a second sealing element disposed on the second sealing surface;
a first housing section contacting the first sealing element and covering the first opening;
a second housing section contacting the second sealing element and covering the second opening; and
a pump unit disposed in the pump chamber and comprising a sac adapted for pumping blood, the pump unit including a pump inlet fluidly communicating with the fluid inlet bore and a pump outlet fluidly communicating with the fluid outlet bore,
wherein the rigid support structure, the first sealing element, the second sealing element, the first housing section, and the second housing section cooperatively fluidly seal the pump chamber and the pump unit from an environment external to the fluid pump housing, with the first sealing element forming a sealed interface between the first housing section and the rigid support structure and the second sealing element forming a sealed interface between the second housing section and the rigid support structure.

21. The VAD fluid pump of claim 20, wherein the first sealing element is parallel to the second sealing element.

22. The VAD fluid pump of claim 20, wherein the first sealing element is non-parallel to the second sealing element.

23. The VAD fluid pump of claim 20, wherein the fluid inlet bore is disposed about an inlet axis, and the fluid outlet bore is disposed about an outlet axis parallel to the inlet axis.

24. The VAD fluid pump of claim 20, wherein the fluid inlet bore is disposed about an inlet axis, and the fluid outlet bore is disposed about an outlet axis non-parallel to the inlet axis.

25. The VAD fluid pump of claim 20, further including an inlet tubing connector attached to the fluid inlet bore, and an outlet tubing connector attached to the fluid outlet bore.

26. The VAD fluid pump of claim 20, wherein the first sealing element and the second sealing element are each configured as a continuous loop of material.

27. The VAD fluid pump of claim 20, wherein the first sealing surface and the second sealing surface are continuous surfaces.

28. The VAD fluid pump of claim 20, wherein a gas inlet is formed in at least one of the first housing section and the second housing section, the gas inlet fluidly communicating with the pump chamber and configured for connection to a gas conduit.

29. The VAD fluid pump of claim 20, wherein at least a portion of the pump unit is deformable for establishing a pulsed flow of fluid from the pump inlet to the pump outlet.

30. The VAD fluid pump of claim 20, further including a one-way inlet valve connected to the pump inlet and a one-way outlet valve connected to the pump outlet.

31. The fluid pump of claim 30, further including an inlet tubing connector interconnecting the fluid inlet bore and the one-way inlet valve, and an outlet tubing connector interconnecting the fluid outlet bore and the one-way outlet valve.

32. The VAD fluid pump of claim 20, wherein the pump unit protrudes out from the first sealing side and the second sealing side of the support structure.

33. A ventricular assist device (VAD) fluid pump, comprising:

a rigid support structure circumscribing a pump chamber, the support structure including a first sealing side, a second sealing side opposite to the first sealing side, a first opening located at the first sealing side, a second opening located at the second sealing side, a first sealing surface circumscribing the first opening, a second sealing surface circumscribing the second opening, a fluid transfer end interposed between the first sealing side and the second sealing side, a fluid inlet bore formed through the fluid transfer end, and a fluid outlet bore formed through the fluid transfer end;

a first sealing element disposed on the first sealing surface;

a second sealing element disposed on the second sealing surface;

a first housing section contacting the first sealing element and covering the first opening;

a second housing section contacting the second sealing element and covering the second opening; and a pump unit disposed in the pump chamber and comprising a sac adapted for pumping blood, the pump unit including a pump inlet fluidly communicating with the fluid inlet bore and a pump outlet fluidly communicating with the fluid outlet bore, wherein the rigid support structure, the first sealing element, the second sealing element, the first housing section, and the second housing section cooperatively fluidly seal the pump chamber and the pump unit from an environment external to the fluid pump housing, with the first sealing element forming a sealed interface between the first housing section and the rigid support structure and the second sealing element forming a sealed interface between the second housing section and the rigid support structure;

a one-way inlet valve connected to the pump inlet and a one-way outlet valve connected to the pump outlet, wherein the one-way inlet valve and the one-way outlet valve are each configured as a hinge-less valve including a plurality of flexible portions movable between an open position and a closed position.

* * * * *